US010485602B2

(12) United States Patent
Geiselhart

(10) Patent No.: US 10,485,602 B2
(45) Date of Patent: Nov. 26, 2019

(54) TEMPERATURE CONTROLLER FOR A CRYOPROBE, CRYOSURGICAL DEVICE HAVING A TEMPERATURE CONTROLLER, AND METHOD FOR REGULATING THE TEMPERATURE OF A CRYOPROBE

(75) Inventor: Franz Geiselhart, Reutlingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 2079 days.

(21) Appl. No.: 13/002,359

(22) PCT Filed: Jun. 10, 2009

(86) PCT No.: PCT/EP2009/004209
§ 371 (c)(1),
(2), (4) Date: Feb. 14, 2011

(87) PCT Pub. No.: WO2010/000376
PCT Pub. Date: Jan. 7, 2010

(65) Prior Publication Data
US 2011/0152848 A1 Jun. 23, 2011

(30) Foreign Application Priority Data

Jul. 2, 2008 (DE) .......................... 10 2008 031 298
Sep. 3, 2008 (DE) .......................... 10 2008 045 563

(51) Int. Cl.
*A61B 18/02* (2006.01)
*A61B 17/00* (2006.01)

(52) U.S. Cl.
CPC .... *A61B 18/02* (2013.01); *A61B 2017/00022* (2013.01)

(58) Field of Classification Search
CPC .... A61B 2018/0212; A61B 2018/0262; A61B 2018/0268; A61B 2018/00863;
(Continued)

(56) References Cited

U.S. PATENT DOCUMENTS 6,387,092 B1 * 5/2002 Burnside et al. ............... 606/32
6,471,694 B1 10/2002 Kudaravalli et al.
(Continued)

FOREIGN PATENT DOCUMENTS

DE 695 32 158 T2 8/2004
DE 602 10 046 T2 11/2006
(Continued)

*Primary Examiner* — Ronald Hupczey, Jr.
(74) *Attorney, Agent, or Firm* — Blank Rome LLP

(57) ABSTRACT

A cryosurgical apparatus with a temperature regulator. For better therapeutic success, it is desirable to set the temperature applied to a cryosurgical instrument as exactly as possible. Conventional apparatuses have corresponding temperature sensors allowing the regulation of the cooling power in the cryosurgical instrument such that the cooling power corresponds to a predefined value. However, the dimensions of some temperature sensors prevent them from being provided within a cryoprobe. Furthermore, suitable temperature sensors are expensive and have low durability. This problem is solved by the disclosed temperature regulator for regulating the temperature of a cryoprobe, which supplies an at least partly liquid refrigerant at a first pressure to an evaporation region such that the coolant evaporates at least temporarily under the presence of a second pressure for cooling a cooling portion of the cryoprobe. A pressure setting means that sets at least the second pressure is also provided.

13 Claims, 1 Drawing Sheet

Figure 1:
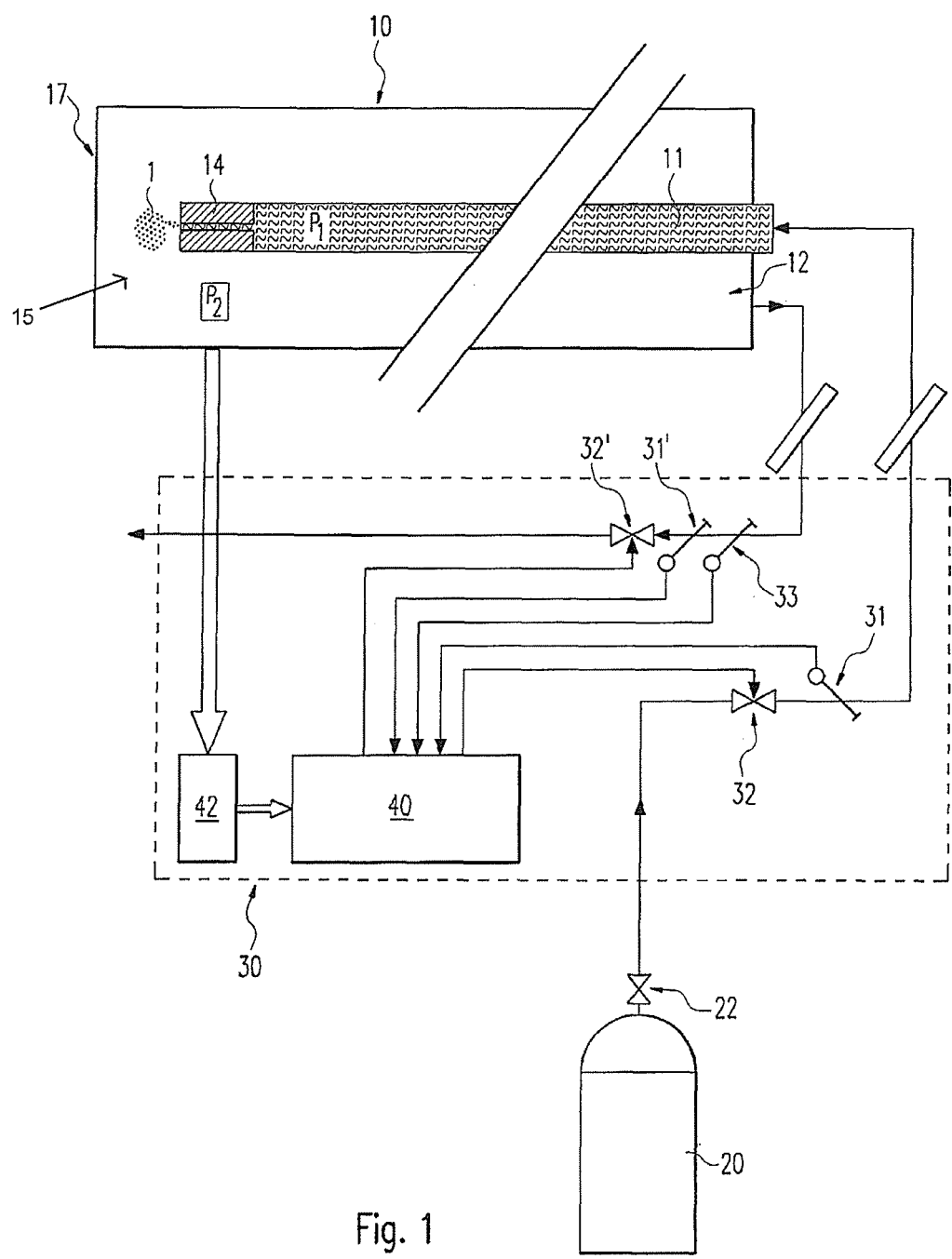

(58) Field of Classification Search
CPC ..........................................................................
A61B 2018/00744; A61B 2018/00791;
A61B 2018/00803; A61B 2018/00714
USPC ..................................................... 606/20, 22
See application file for complete search history.

(56) References Cited

U.S. PATENT DOCUMENTS

| | | | |
|---|---|---|---|
| 7,004,936 B2* | 2/2006 | Ryba et al. | ...................... 606/20 |
| 2003/0220634 A1 | 11/2003 | Ryba et al. | |
| 2006/0004350 A1 | 1/2006 | Ryba | |
| 2007/0027444 A1 | 2/2007 | Levin | |
| 2012/0253337 A1* | 10/2012 | Watson | ........................... 606/21 |

FOREIGN PATENT DOCUMENTS

| | | |
|---|---|---|
| DE | 603 06 281 T2 | 4/2007 |
| EP | 1 398 002 A1 | 3/2004 |
| JP | 2004-275732 A | 10/2004 |
| WO | WO 99/56640 A1 | 11/1999 |
| WO | WO 00/42932 A1 | 7/2000 |
| WO | WO 03/028569 A1 | 4/2003 |

\* cited by examiner

TEMPERATURE CONTROLLER FOR A CRYOPROBE, CRYOSURGICAL DEVICE HAVING A TEMPERATURE CONTROLLER, AND METHOD FOR REGULATING THE TEMPERATURE OF A CRYOPROBE The invention relates to a temperature regulator for regulating the temperature of a cryoprobe according to claim 1, to a cryosurgical apparatus with a temperature regulator of this type according to claim 10 and to a method for regulating the temperature of a cryoprobe.

Cryosurgical apparatuses are known. They comprise a cryosurgical instrument, a fluid source and a controller for setting the cooling power which is provided on the cryosurgical instrument. Either a cold steam system or the Joule-Thomson effect is used for providing the cooling power.

The Joule-Thomson effect occurs when a real gas or gas mixture experiences a change in temperature as a result of restriction (change in pressure). If a gas is restricted, for example if a restrictor is used or a different obstacle integrated, the gas expands. This means that the volume taken up by the gas after the obstacle increases. In this case, the average particle spacing increases, causing the temperature of the gas to fall.

The cold steam system utilises the property of substances of having different boiling or condensation temperatures at different pressures. The substances which are used and preferred are called refrigerants. The working range of a cold steam system is delimited by the achievable boiling or condensation temperatures of the refrigerant. Conventionally, a liquefied refrigerant is injected under high pressure into an evaporation chamber in which the pressure is much lower. The boiling point of the corresponding refrigerant depends on the one hand on the refrigerant used, on the one hand on the pressure prevailing in the evaporation chamber. Therefore, if the evaporation chamber yields a boiling point that is above the prevailing temperature in the evaporation chamber, the refrigerant at least partly evaporates and removes heat energy from the system. The evaporated refrigerant is removed again through a discharge run and either re-condensed or disposed of.

For effective and advantageous use of cryosurgical instruments, it is necessary to be able to set the temperature of the probe or a part thereof to a predefined value and to keep it constant at this value. In cryosurgery, it is thus possible to achieve, for example, a reproducible tissue effect in identical indications. It is also desirable to be able to vary the temperature of the tip of the probe for different indications in order to achieve the optimum tissue effect in each case.

In order to be able to bring about exact regulation of the cooling power and the temperature prevailing at the tip of the probe, modern cryosurgical apparatuses comprise temperature regulators.

For this regulation, it is necessary to determine the temperature at the tip of the probe. Miniature sheathed thermocouples are currently used as temperature sensors. These are relatively expensive, assembly thereof is complex and the durability is relatively low owing to the low mechanical stability and the susceptibility to corrosion. For very thin probes, there are no thermocouples having an appropriate design. There are therefore specific probes (for example endocryoprobes and intravitreal probes) only without temperature regulation.

Alternatively, use is made of cryosurgical apparatuses, the instruments of which contain reversible restrictors in the return run. For example, these restrictors have three adjustable stages. The temperature may be regulated in a semi-constant fluid source between the individual adjustable stages. Reference values may be determined by repeatedly using the instruments or by measuring out the cooling power. The reference values determined in this way are relatively inaccurate and fluctuate as a function of the field of use. New measurements also have to be carried out for all of the instruments used. This is very costly.

Starting from this prior art, the object of the present invention is to provide an improved temperature regulator for regulating the temperature of a cryoprobe. In particular, a temperature regulator is to be disclosed that can be used in all cryoprobes, irrespective of their design.

Furthermore, a corresponding cryosurgical apparatus and a method for regulating the temperature of a cryoprobe shall be disclosed.

According to the invention, this object is achieved by a temperature regulator according to claim 1, a cryosurgical apparatus according to claim 9 and a method according to claim 11.

In particular, the object is achieved by a temperature regulator for regulating the temperature of a cryoprobe, which supplies a refrigerant at a first pressure to an evaporation region in such a way that the coolant evaporates at least temporarily under the presence of a second pressure for cooling a cooling portion of the cryoprobe, a pressure setting means being provided that sets at least the second pressure in the evaporation region for regulating the temperature of the cryoprobe. A basic idea of the present invention therefore consists in setting the pressure in the evaporation region in such a way as to produce for the refrigerant used a boiling point which is substantially the same as or close to the desired target temperature in the cryoprobe. Once the cryoprobe has reached this target temperature, there is therefore no more evaporation and no cooling power is produced in the cryoprobe. If the temperature in the evaporation region is above the set boiling point, this leads to evaporation which withdraws heat energy from the evaporation region and thus from the cryoprobe. There is thus no need to determine the present temperature in the evaporation region or on the cryoprobe, as the system is self-regulating at the preset boiling point.

Whereas the term "refrigerants" in the narrower sense includes heat produced by evaporation at low pressure and low temperature, this is carried out in a cold mixture chemically by way of a mixing and dissolving reaction. The regeneration is therefore carried out in cold mixtures by way of segregation. In this application, the term "refrigerant" is to be understood in its more general meaning, i.e. also including cold mixtures.

The pressure setting means can comprise at least a first pressure transducer for measuring the second pressure and at least one adjustable valve which are connected via a regulating means for regulating the second pressure. As the boiling point is directly dependent on the present pressure, the temperature of the cryoprobe may be set by defining a specific pressure in the evaporation region. The temperature can therefore be regulated by means of a valve and a corresponding pressure transducer. The regulating means is therefore embodied in such a way that it sets, depending on the defined temperature, a constant pressure in the evaporation region. Regulating the temperature via a pressure transducer valve has the further advantage that these elements do not necessarily have to be arranged within the cryoprobe. It is conceivable to provide the pressure transducer and the valve on the discharge run of the cryoprobe. Furthermore, these elements can be arranged for example within a handle of the cryoprobe. Compared to the arrangement with a temperature sensor, it is not necessary for the elements to be arranged directly in or on the evaporation region which conventionally is spatially highly delimited.

The temperature regulator can comprise at least one pressure reducer for regulating the second pressure.

The temperature regulator can comprise a flow measuring means for determining a flow occurring as the refrigerant flows out of the evaporation region and a compensation means for including a flow resistance opposing the outflow in the measuring and/or setting of the second pressure. If a pressure transducer arranged set apart from the evaporation region is opted for, then it is helpful to take account of a flow resistance which occurs between the measuring region and the evaporation region. At low temperatures, if the returning gas has a low pressure and thus a large specific volume, the flow resistance is high and correction is therefore especially important at this point. In addition, the boiling-point curve runs particularly steeply in this temperature range and thus a small error in the measurement of the pressure results in a large error with regard to the temperature. The flow measuring means can comprise, for determining the flow, a second pressure transducer for detecting the first pressure. It is for possible to conclude the flow resistance from the pressure differential in the admission run and in the discharge run. Alternatively, the gas through-flow can provide at a suitable point information concerning the flow resistance to be taken into account. The compensation means can comprise a data input device for inputting flow resistance data of the cryoprobe. As the flow resistance is dependent on the configuration of the respective cryoprobe, in particular on the cross section of the return run, the flow resistance can be predetermined and be input manually or automatically via a data input device.

For example, the data input device can comprise a data memory containing flow resistance data of a large number of cryoprobes. This makes determining the flow resistance much easier.

The data input device can comprise an apparatus identification means for identifying a connected cryoprobe. It is thus conceivable for the temperature regulator to automatically identify a connected cryoprobe and to read out corresponding flow resistance data from a data memory. These flow resistance data can be used in order to be taken into account in the measurement and/or setting of the second pressure.

The object is also achieved by a cryosurgical apparatus, comprising a cryoprobe with a probe shank and a temperature regulator, as described hereinbefore. The advantages are obtained in a similar manner as has been previously presented.

The cryoprobe can comprise at least a first pressure transducer which, for detecting the second pressure, is arranged at or close to the proximal end of the probe shank. Thus, the said pressure setting device can be arranged where there is sufficient space for the corresponding elements, for example valves or pressure transducers.

The object is also achieved by a method for regulating the temperature of a cryoprobe, wherein the cryoprobe has an evaporation region for evaporating a refrigerant and the method includes the following steps:
 determining at least one pressure of the refrigerant in the evaporation region;
 setting the pressure to a predetermined value in order to regulate the temperature of the cryoprobe.

In the method, a central idea therefore consists in ensuring the temperature regulation based on the setting of a specific pressure in the evaporation region. The temperature is thus regulated indirectly via the pressure.

The at least one pressure can be determined by means of a pressure transducer in the cryoprobe at the proximal end thereof or during the removal of the refrigerant from the cryoprobe. When determining the pressure, there is therefore no obligation to measure the pressure directly in the evaporation region.

The flow resistance must be taken into account in the method too.

The invention will be described hereinafter based on a few exemplary embodiments which will be illustrated in greater detail by means of a diagram, in which:

FIG. 1 is a schematic view of a cryoprobe with a temperature regulator.

The cryosurgical apparatus according to the invention comprises a fluid source 20 for providing a refrigerant 1 at a predetermined pressure. The refrigerant 1 is supplied to a cryoprobe 10 via a temperature regulator 30. An admission run 11, which leads the refrigerant 1 into a region close to the tip of 17 of the probe, extends inside the cryoprobe 10. Within the admission run 11, the refrigerant has a first pressure $P_1$ which is sufficiently high that the resulting refrigerant-specific boiling point is much lower than the temperature present in the cryoprobe 10. The refrigerant 1 therefore maintains its liquid state. The refrigerant 1 is issued into an evaporation region 15 arranged within the cryoprobe 10 via a nozzle 14 at the distal end of the admission run 11. The second pressure $P_2$ which is present here is much lower than the first pressure $P_1$. A lower boiling point is thus obtained in a refrigerant-specific manner. The refrigerant 1 evaporates as a function of the temperature present in the cryoprobe 10 and withdraws heat energy from the cryoprobe. Alternatively, the refrigerant 1 can be supplied in gas form at maximum operating pressure (removal of gas on the boiling-point curve) in such a way that the gas is converted during cooling, as a result of the Joule-Thomson effect on the nozzle 14, into a two-phase mix. The liquid component boils at the inner surface of the probe head or the tip 17 of the probe in the evaporation region 15.

The refrigerant 1 or gas is then returned via a discharge run 12 within the cryoprobe 10 into the temperature regulator 30 and is from there disposed of or re-prepared. For this purpose, the discharge run 12 is fluidically connected to the evaporation region 15 and the temperature regulator 30.

As a result of the regulation of the second pressure $P_2$, the boiling temperature can be set in accordance with a predefined value. It is therefore possible to establish a direct correlation between the second pressure $P_2$ and the cooling power of the cryoprobe 10.

In order to effectively regulate the temperature of the cryoprobe 10, the temperature regulator 30 comprises a controller 40 and also an admission run pressure transducer 31, a discharge run pressure transducer 31', an admission run proportional valve 32, a discharge run proportional valve 32' and a through-flow sensor 33. The admission run pressure transducer 31 emits signals allowing the controller 40 to conclude the first pressure $P_1$ in the admission run 11. For this purpose, the admission run pressure transducer 31 is arranged on the admission run 11. The discharge run pressure transducer 31 is accordingly arranged on the discharge run 12 and emits signals allowing the controller 40 to determine the second pressure $P_2$ within the evaporation region 15. In order to be able to take account of the pressure drop which occurs as the refrigerant 1 flows out of the evaporation region 15 via the discharge run 12, a pressure flow sensor 33, by means of which the controller 40 can conclude the present flow resistance, is also located on the discharge run 12. Thus, the controller 40 can correct the pressure measured using the discharge run pressure transducer 31 in consideration of the flow resistance and determine a correspondingly revised pressure $P_2$.

This correction is especially important if the cryoprobe 10 is operated at low temperatures. The returning gas or the refrigerant 1 then has a very low pressure $P_2$ and thus a large specific volume, resulting in a high flow resistance. In addition, the boiling-point curve of conventional refrigerants 1 runs particularly steeply in this temperature range and thus a small error in the calculation of the second pressure $P_2$ results in a marked deviation in the setting of the temperature in the cryoprobe 10.

An advantage of the present invention is the fact that the sensors and transducers for determining the first pressure $P_1$ and/or the second pressure $P_2$ do not have to be arranged in or close to the evaporation region 15.

These sensors or transducers can be attached in the discharge run 12 or admission run 11 or to the proximal end thereof. A design of cryoprobes 10 having a much smaller diameter is thus conceivable.

In a second exemplary embodiment, the flow resistance can be determined solely based on the admission run pressure transducer 31 and the discharge run pressure transducer 31'. For this purpose, it is necessary to provide apparatus-specific data via the cryoprobe 10 which is connected to the temperature regulator 30. These data comprise for example the cross section of the nozzle 14. Alternatively, measurements of the flow resistance can be carried out and tabularised in the laboratory as a function of the first and/or second pressure $P_1$, $P_2$. In order to be able to allocate the apparatus-specific data to a specific cryoprobe 10, one exemplary embodiment includes a data input device. This data input device has a memory for storing the apparatus-specific data and an apparatus recognition means allowing it to select a specific type of cryoprobe 10. As soon as a specific cryoprobe 10 has been selected, the controller 40 calculates the apparatus-specific flow resistance as a function of the pressure ratios and the stored apparatus or instrument-specific data.

Alternatively, the data input device 42 can carry out automatic detection of the connected apparatus type.

This automatic recognition can be carried out, for example, by reading out a serial number stored in an RFID tag attached to the cryoprobe 10.

The person skilled in the art will be familiar with numerous further methods as to how a corresponding identification of the connected cryoprobe 10 may be facilitated. These include determining various characteristic variables in a test phase of the cryoprobe 10 preceding an operation, reading-out a Bluetooth tag or scanning-in a barcode.

In order to be able to determine the second pressure $P_2$ in as error-tolerant a manner as possible, it is conceivable to determine the flow resistance according to the method in the first exemplary embodiment and that in the second exemplary embodiment. Alternatively, just one of the two methods may be applied.

It will be obvious to the person skilled in the art that the method according to the invention for regulating the temperature of the cryoprobe 10 may be carried out also if just one discharge run pressure transducer 31' and one discharge run proportional valve 32' are present.

The controller 40 can therefore implement, after determining the second pressure $P_2$, a regulating loop in which the discharge run proportional valve 32', which is connected to the discharge run 12, is set in such a way that the pressure $P_2$ reaches a predefined value. This value corresponds, depending on the refrigerant 1 used, to a specific boiling or evaporation temperature. This temperature can be input to the controller 40 through the operating unit which is operated by the doctor carrying out the treatment.

The controller 40 can set via the optional admission run proportional valve 32 the first pressure $P_1$ which can be determined via the admission run pressure transducer 31. It is thus for example possible to regulate, via the admission run proportional valve 32, the amount of the refrigerant 1 introduced into the cryoprobe 10. Furthermore, the cooling power, which is achieved by means of the Joule-Thomson effect, can be defined by setting the pressure differential between the first pressure $P_1$ and the second pressure $P_2$.

The fluid source 20 also has an optional fluid source valve 22 allowing manual setting of the input pressure at which the refrigerant 1 is introduced into the temperature regulator 30.

In summary, it should be noted once more that the invention sets the second pressure $P_2$ for regulating the cooling power of the cryoprobe 10.

The specific boiling point of a refrigerant 1 is dependent, as is known, on the prevailing pressure and the present temperature. At a predefined second pressure $P_2$, the refrigerant 1 therefore boils only up to a specific temperature. If a lower temperature is already present in the evaporation region 15, the refrigerant 1 does not boil. Accordingly, no heat is withdrawn from the system, based on the change of state. During a continuous supply of refrigerant 1 at a constant second pressure $P_2$, the corresponding specific temperature is therefore set in the evaporation region 15.

REFERENCE NUMERALS

1 Refrigerant
10 Cryoprobe
11 Admission run
12 Discharge run
14 Nozzle
15 Evaporation region
17 Tip of the probe
20 Fluid source
22 Fluid source valve
30 Temperature regulator
31 Admission run pressure transducer
31' Discharge run pressure transducer
32 Admission run proportional valve
32' Discharge run proportional valve
33 Through-flow sensor
40 Controller
42 Data input device
$P_1$ First pressure
$P_2$ Second pressure

The invention claimed is:

1. A temperature regulator for regulating the temperature of a cryoprobe, the temperature regulator configured to supply a refrigerant at a first pressure to an evaporation region such that the coolant evaporates at least temporarily under the presence of a second pressure for cooling a cooling portion of the cryoprobe, said temperature regulator comprising:

pressure setting means that is used by the temperature regulator to set the second pressure in the evaporation region to a target pressure for regulating the temperature of the cryoprobe based on a target temperature, wherein the target temperature is manually input at an operating unit, the pressure setting means comprising at least one adjustable valve arranged downstream of the evaporation region for regulating the second pressure; and flow measuring means for determining a flow occurring as the refrigerant flows out of the evaporation region, wherein the temperature regulator uses the determined flow when controlling the at least one adjustable valve to set the second pressure to the target pressure.

2. The temperature regulator according to claim 1, wherein the pressure setting means further comprises at least a first pressure transducer for measuring the second pressure, the at least a first pressure transducer and the at least one adjustable valve being connected by regulating means for regulating the second pressure.

3. The temperature regulator according to claim 1, further comprising at least one pressure reducer for regulating the second pressure, wherein the pressure setting means sets the second pressure using the at least one pressure reducer.

4. The temperature regulator according to claim 1, wherein the flow measuring means comprises a second pressure transducer for detecting the first pressure.

5. The temperature regulator according to claim 1, further comprising:

compensation means for including a flow resistance opposing the outflow in the measuring and/or setting of the second pressure.

6. The temperature regulator according to claim 5, wherein the compensation means comprises a data input device for inputting flow resistance data of the cryoprobe.

7. The temperature regulator according to claim 6, wherein the data input device comprises a data memory containing flow resistance data of a plurality of cryoprobes.

8. The temperature regulator according to claim 6, wherein the data input device comprises an apparatus identification unit for identifying a connected cryoprobe.

9. The temperature regulator according to claim 1, further comprising expansion means connected upstream of the evaporation region for at least partly expanding the refrigerant.

10. A cryosurgical apparatus comprising:
a cryoprobe with a probe shank; and
a temperature regulator according to claim 1 connected to the cryoprobe.

11. The cryosurgical apparatus according to claim 10, wherein the pressure setting means comprises at least a first pressure transducer, for detecting the second pressure, which is arranged at or close to the proximal end of the probe shank.

12. A system for regulating the temperature of a cryoprobe, the system comprising:
an operating unit configured to accept manual input for defining a target temperature; and
a temperature regulator configured to receive the target temperature from the operating unit and to supply a refrigerant at a first pressure to an evaporation region of the cryoprobe such that the coolant evaporates at least temporarily under the presence of a second pressure for cooling a cooling portion of the cryoprobe, said temperature regulator configured to determine a target pressure based on the target temperature and comprising:

pressure setting means that is used by the temperature regulator to set the second pressure in the evaporation region to the target pressure for regulating the temperature of the cryoprobe based on the target temperature, the pressure setting comprising at least one adjustable valve arranged downstream of the evaporation region for regulating the second pressure; and flow measuring means for determining a flow occurring as the refrigerant flows out of the evaporation region, wherein the temperature regulator uses the determined flow when controlling the at least one adjustable valve to set the second pressure to the target pressure.

13. A system for supplying a refrigerant to a connected cryoprobe and for regulating the temperature of the connected cryoprobe, the cryoprobe having an evaporation region for evaporating the refrigerant, the system comprising:

an operating unit configured to accept manual input for defining a target temperature; and
a temperature regulator comprising:
an admission run pressure transducer for measuring a first pressure in an admission run of the connected cryoprobe
a discharge run pressure transducer for measuring the pressure in a discharge run of the connected cryoprobe,
a discharge run proportional valve connected to the discharge run of the connected cryoprobe;
a through-flow sensor for measuring the through-flow of refrigerant in the discharge run; and
a controller configured to receive signals from the discharge run pressure transducer and the through-flow sensor, to calculate based on the receiving signals from the discharge run pressure transducer and the through-flow sensor a second pressure in the evaporation region, to calculate based on the target temperature a target pressure at which the refrigerant should evaporate in the evaporation region to establish the target temperature in the evaporation region, to compare the target pressure with the second pressure and to adjust the discharge run proportional valve such that the target pressure is reached in the evaporation region, thereby regulating the temperature of the cryoprobe to the target temperature.

* * * * *